Figure 1:
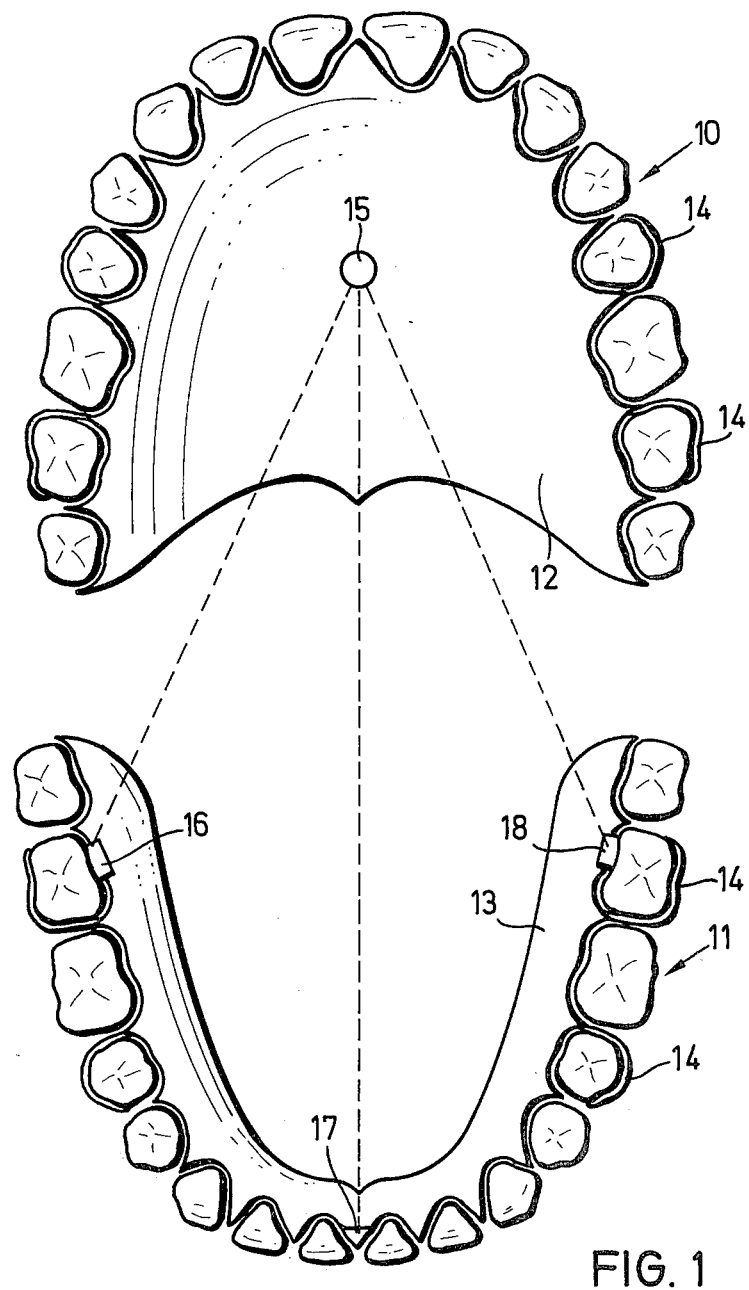

United States Patent [19]

Becker et al.

[11] 4,330,276
[45] May 18, 1982

[54] PROCESS AND APPARATUSES FOR REPRODUCING JAW MOVEMENTS

[75] Inventors: Günter Becker, Aachen; Horst Weiden, Stolberg, both of Fed. Rep. of Germany

[73] Assignee: Becker Dental-Labor GmbH, Aachen, Fed. Rep. of Germany

[21] Appl. No.: 184,410

[22] Filed: Sep. 5, 1980

[30] Foreign Application Priority Data

Sep. 8, 1979 [DE] Fed. Rep. of Germany ....... 2936328

[51] Int. Cl.³ .............................................. A61C 19/04
[52] U.S. Cl. ......................................... 433/69; 433/55
[58] Field of Search ...................... 433/55, 54, 61, 68, 433/69, 73; 128/777

[56] References Cited

U.S. PATENT DOCUMENTS 3,381,377  5/1968  Grayson ................................ 433/27
3,390,459  7/1968  Seidenberg .......................... 433/27
4,234,306  11/1980  Hamada et al. ....................... 433/55

*Primary Examiner*—Robert Peshock
*Attorney, Agent, or Firm*—Spensley, Horn, Jubas & Lubitz

[57] ABSTRACT

To reproduce jaw movements, electric distance measuring devices are fixed at the lower jaw and the upper jaw in the mouth of a patient to measure, with relative movements between upper and lower jaws, the distances between defined points of the two jaws and to supply the data to a memory. In accordance with the recorded measuring data a mobile portion of an articulator carrying a jaw model is so guided that it reproduces the recorded sequence of motion, the combinations of the measured distances between the defined points of lower jaw and upper jaw being repeated in the same way as in the measuring operation.

20 Claims, 5 Drawing Figures

PROCESS AND APPARATUSES FOR REPRODUCING JAW MOVEMENTS

The invention relates to a process for reproducing jaw movements comprising
- fixing in a patient's mouth at the upper and lower jaws auxiliary devices which are recording measuring data as a result of relative movements between the upper and lower jaws and
- guiding a mobile portion of an articulator carrying a jaw model corresponding to the recorded measuring data, as well as apparatuses for performing the process.

The teeth of upper and lower jaws, in an ideal situation, are coordinated to each other specifically in space when the mouth is closed. If the jaws are pressed against each other, the teeth should find a uniform mutual support in several points of pressure. If the teeth structure is imperfect, there are formed local pressure marks upon the compression of the jaws which marks are due to an unequal load on the teeth. Such a false load on the teeth may entail a general bad feeling and paradontosis as well as other diseases.

Thus, it will not do for the preparation of artificial denture to fix the artificial tooth at the corresponding point in the jaw. The surface contour of the tooth, its height as well as the position of the teeth will play an important part. To enable the artificial tooth to take up part of the force developed during chewing and other stresses acting on the jaws, the relative movements between upper and lower jaws of the corresponding patient have to be taken into account for the design of the tooth. The development of movements between lower jaw and upper jaw is quite different with each patient. This is due to the fact that the joints of the jaws are formed differently. The shape of the jaw joints does not only dictate the curve of the motion, when the mouth is opened or closed, but it also dictates the lateral movements of the lower jaw. The dental technician, who prepares an artificial denture cannot use a general model to fit a tooth and which represents a coordination of lower and upper jaws, because the anatomic form of the jaw joint and the jaw movements are different with each person.

It has been known to prepare individual models of lower and upper jaws of a patient and to fit them in an articulator which assumes the function of the jaw joint. The articulator can be adjusted in different ways so as to imitate as exactly as possible the curve of motion of the jaw joint of the corresponding patient. However, the jaw joint of the corresponding patient must be measured first before the articulator can be adjusted accordingly. To this end, impressions of the two jaws of the patient are made, and reference plates are prepared in conformity therewith which are fastened in the mouth of the patient. The reference plates are provided with bars projecting out of the mouth of the patient to be secured to an apparatus mounted in front of the face of the patient and the jaw movements are transferred to said apparatus. At the apparatus and near the ears of the patient, there are recording pencils to mark corresponding cards. After having adjusted the measuring instrument, the dentist moves the patient's lower jaw in different directions and the pencils mark curves on the cards accordingly. By means of a complicated process, the curves are evaluated to adjust the corresponding articulator of the dental technician accordingly.

The known process for imitating the movements of the jaw joints calls for involved preparations and measurements. Already adjusting the measuring instruments and performing the measurements always takes several hours. The evaluation of the record cards and the adjustment of the articulator are also very involved and may cause errors of transmission, of measurement and adjustment. After all, the measurement is relatively inaccurate because, due to the reference plates and the bars projecting out of his mouth, the patient cannot close his mouth so as to press the teeth against each other. As for the movements to be recorded, he is greatly restricted. Furthermore, an additional inaccuracy is caused in that the lower jaw of the patient is moved by the dentist. As a matter of fact, the influence of the muscles which are excluded in this case, also plays an important part for the sequence of motions. In other words, the movements guided by the dentist entail another sequence of motions than the natural movement caused by the muscles of the patient. Taken as a whole, in the known process for reproducing the jaw movements, not only the measuring process but also the articulator movement are inaccurate. The measuring process and the adjustment of the articulator are complicated and susceptible to mistakes and interferences.

It is the object of the invention to provide a process of the type mentioned at the outset hereof which permits a true reproduction of the relative movements between the upper jaw and the lower jaw, the measurement being performable within no time and no high requirements are demanded either from the dentist or from the dental technician.

To solve said problem, it is provided according to the invention that electric distance measuring devices are arranged in the mouth of the patient to measure the distances between defined points at the upper jaw and the lower jaw during their movement to supply the data to a memory and that the mobile portion of the articulator is controlled in accordance with the stored data so that the recorded sequence of motions is reproduced, the combination of the distances measured between the defined points of lower jaw and upper jaw being repeated in the same manner as in the measuring operation.

It is only necessary that thin cables extend out of the mouth of the patient to lead to the space measuring devices. Thus, the possible movements of the jaws of the patient are practically not hampered at all. During the measuring operation he makes specific movements of his jaws as instructed by the dentist. The signals supplied by the distance measuring devices are stored digitally in the memory. In the laboratory of the dental technician, the data are recalled to control therewith the articulator at which models of the lower jaw and of the upper jaw of the patient are mounted. The models subsequently make the same movements as made before by the patient. By means of said movements, the dental technician can study the relative jaw positions and the wax pattern of the artificial tooth to be set can be exactly adapted to the demands of the patient.

It is a particular advantage that the jaw movements during the measuring operation can be performed by way of the own muscle action of the patient, so that the influence of the muscles on the sequence of motions can be considered simultaneously. By the exact reproduction of the jaw movements in the articulator, the dental technician will get a very precise idea of the sequence of motions of the corresponding patient.

In an advantageous further embodiment of the invention, individual jaw plates are prepared for the upper and lower jaws of the patient to secure thereto the distance measuring devices for the measuring operation. For the reproduction, the same jaw plates are placed in patterns of the upper jaw and of the lower jaw, and the distance values measured in the measuring operation are adjusted again in the reproducing operation without the need of conversion. By this means, it is certain that with a sufficiently exact distance measurement exactly the same jaw positions can be taken again in the articulator. The same jaw plates being used for the measuring as for the reproducing operation, no reference points must be determined for the patient because the space measuring devices are fixed at the jaw plates after all.

An apparatus for performing the process of the invention is characterized in that at the jaw plates for the upper jaw and the lower jaw, at least one distance measuring device is provided to measure the distance between two defined points of both jaw plates. The jaw plates only serve for fixing in a defined mechanical manner the members of the space measuring devices at the jaws. The distance measuring device may consist of a transmitter and receiver which are to be fastened to a corresponding jaw plate at a jaw. It is also possible to fit a combined transceiver device at one jaw and a reflector at the other jaw. As distance measuring devices, inductive measuring instruments can be used which indicate the distance of a metal element from a coil. Distance measuring devices to measure the distances under consideration with sufficient accuracy are known.

Preferably, at least three distance measuring devices are provided. They may consist of one common transmitter secured to the one jaw plate, and of at least 3 receivers secured to the other jaw plate. With a relative movement of the two jaw plates, the distances of all three receivers change accordingly. The latter being fitted in the form of an equilateral triangle, and the transmitter being above the center of said triangle, all sequences of motions can be determined rather exactly.

The articulator by which plaster models of the jaws are conducted in accordance with the movements of the original jaws preferably has a stationary plate for the model of the upper jaw and a mobile plate for the model of the lower jaw which plate is movable in several degrees of freedom by means of a control unit. The control unit for the mobile plate may be connected to a comparator which compares the space data determined during the measuring operation and stored in a memory, with the space data measured at the articulator to adjust deviations to zero by a corresponding actuation of the control unit.

Alternatively, the control unit may be connected to a computer circuit, converting the space data determined during the measuring operation into control signals for different drive assemblies to move the mobile plate. In such a case, there does not exist a closed feedback control system in which a deviation is made zero, but the space data determined during measuring are converted to be used as guide data for the drive assemblies of the articulator.

In an advantageous embodiment of the invention, the mobile plate of the articulator is connected via linear drives with a base plate. Similar systems have been known from flight simulators.

Figure 2:
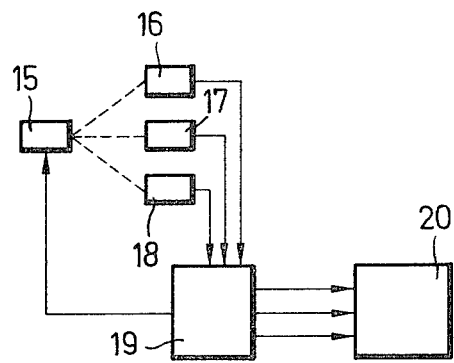
Figure 3:
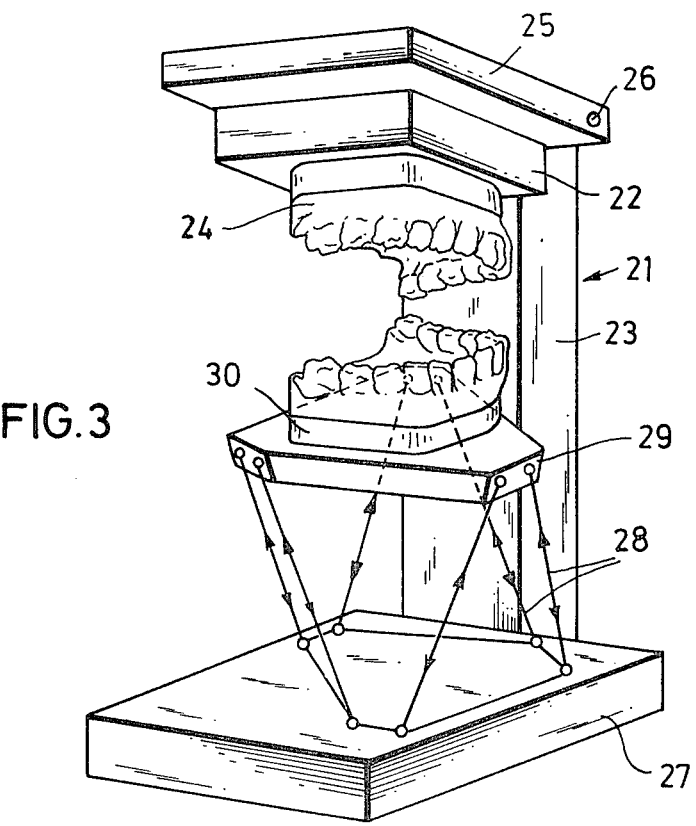
Figure 4:
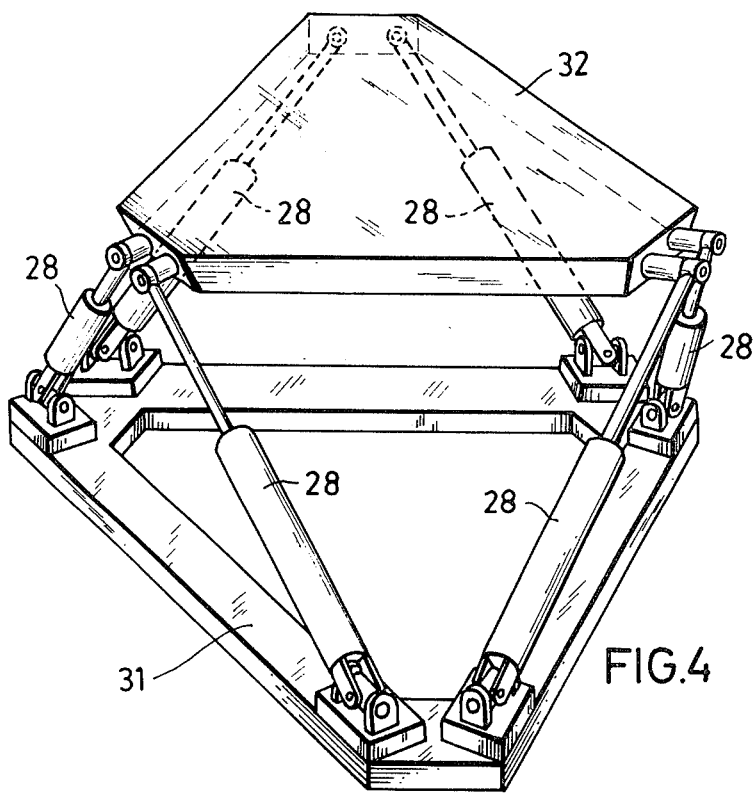
Figure 5:
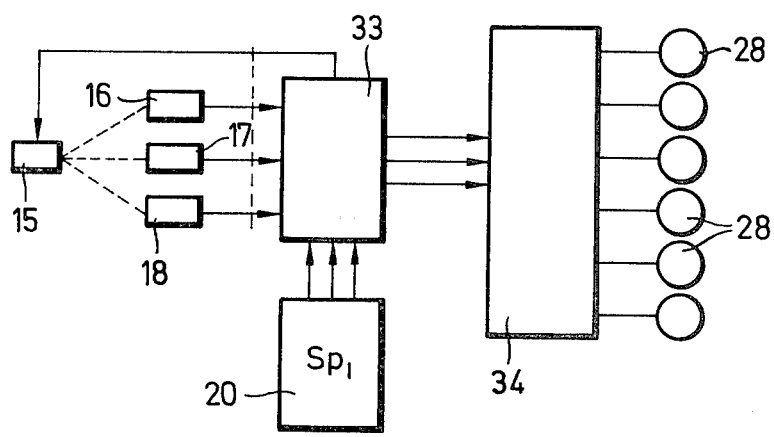

With reference to the Figures, one embodiment of the invention will be explained hereinafter more closely:

FIG. 1 is a schematic view of two jaw plates carrying three space measuring devices and being fixed in the mouth of a patient, FIG. 2 is a block diagram of the recording device for the distance data, FIG. 3 is a perspective view of an articulator, FIG. 4 is a perspective view of the drive assembly of the articulator and FIG. 5 is a block diagram of the control circuit for the drive assembly of the oscillator.

In FIG. 1, the upper jaw of a patient is marked with the reference numeral 10, the lower jaw with 11. First off, the dentist prepares an alginate impression of upper jaw and of the lower jaw. Said impressions are used by the dental technician to prepare a jaw plate 12 for the upper jaw and a jaw plate 13 for the lower jaw. The jaw plates 12 and 13 are provided with wire clamps 14 by which they can be clamped at the teeth so that they are firmly seated at the corresponding jaw or the row of teeth and a displacement or unintentional detachment is impossible. As evident from FIG. 1, the jaw plate 12 is a palate base which substantially covers and fits the palate area, while the the jaw plate 13 for the lower jaw consists of an U-shaped element leaving space for the tongue. The jaw plates 12 and 13 made of plastics are adapted to the jaws and do not interfere with the jaw movements so that the patient can completely close and open his mouth and also other jaw movements can be freely made.

More or less in the center of the jaw plate 12 of the upper jaw, there is provided a transmitter 15 supplying short pulses at regular intervals. Corresponding receivers 16, 17, 18 are at the jaw plate 13 for the lower jaw. The three receivers 16,17,18 are provided in the corners of an approximately equilateral triangle. When the mouth is closed, the transmitter 15 is nearly above the center of the equilateral triangle formed by the receivers 16,17,18. The distance between transmitter and receiver can be determined by the transit time of the transmitter signals from the transmitter 15 to the corresponding receivers 16,17,18. The transmitter 15 thus forms together with each of the receivers 16,17 and 18 one space measuring device.

Trigger lines for the transmitter and the signal output lines for the receivers 16,17,18 or the supply lines are not shown in FIG. 1. They are conducted out of the open mouth in the form of a thin conductor bundle.

In FIG. 2, a trigger line for the transmitter 15 and the signal output lines of receivers 16, 17 and 18 are shown. The receiver 15 is triggered by a control unit 19. As soon as the transmitter signals are received from the receivers 16,17 and 18, they supply corresponding signals to the control unit 19. The control unit 19 forms the distance values from the transit time between the transmission of the pulses and the arrival of the received signals. Said values are converted into a digital form and supplied to a memory 20. The memory 20 may be for inst. an electric or magnetic memory, e.g. a magnetic tape memory.

The measuring system shown in FIG. 2 is in the dentist's office. He fits the jaw plates 12 and 13 in the mouth of his patient and asks him to make special jaw movements during which the transmission of the corresponding distance values is performed either continuously or at shortly successive scanning moments from the control unit 19 to the memory 20. In other words, the sequence of motions is recorded continuously or quasi-continuously in memory 20.

In FIG. 3, an articulator 21 is illustrated which is in the office of the dental technician. At its supporting frame 23, the articulator 21 has a firmly adjustable receiving unit 22 for the plaster model 24 of the upper jaw. The receiving unit 22 is secured to a substantially horizontal plate 25 which, at the frame 23, can be swivelled about a horizontal axis 26 and can be fixed.

At the lower part of frame 23, there is provided a base plate 27 above which a receiving unit 29 for the plaster model 30 of the lower jaw is arranged of six linear motors 28 in total. By the controlled adjustment of the linear motors 28 the receiving unit 29 with the plaster model 30 can be moved corresponding to 6 degrees of freedom. The plaster model 30 for the lower jaw thus may perform protrusion movements, lateral movements, opening and closing movements as well as parallel displacements individually or in combination, due to the corresponding control of the linear motors 28. Concerning the linear motors, use may be made e.g. of spindle drives or hydraulic or pneumatic piston cylinder units. The drive means with linear motors 28 is illustrated in a perspective view of FIG. 4. It comprises a triangular lower frame 31 and a triangular upper frame 32.

In the mid-position in which the two frames extend in parallel, the corners of the upper frame 32 are above the center points of the sides of the lower frame 31. From each corner of the lower frame 31, two linear motors 28 consisting for inst. of piston cylinder units extend to the adjacent corners of the upper frame 32.

The corresponding jaw plates 12 or 13 with the transmitter 15 and the receivers 16,17,18 may be mounted in the plaster models 24 and 30 of the lower jaw and of the upper jaw. The measuring device of the articulator is shown in FIG. 5. The transmitter 15 and the receivers 16,17,18 are connected to a control unit 33 in the same way as in the receiving device according to FIG. 2. Moreover, a memory 20 is connected to the control unit 33. The control unit 33 now compares the actual values of the measured distances with the desired values supplied from the memory 20 and gives the difference signals for each measured distance to a control unit 34 for the linear drives 28. The control unit 34 converts the deviations into digits for the linear drives 28 which, as a result thereof, achieve the adjustment of the lower plaster model in the way in which the patient previously had held his lower jaw in relation to his upper jaw. By this means, the sequence of motion executed in the dentist's practice is reproduced with the articulator.

The elements shown in FIG. 5 at the left side of the dashed line can be omitted. In other words, the jaw plates 12 and 13 need not be absolutely mounted into the plaster models 24 and 30 for the evaluation of the situation. In this case, there is only a follow-up adjustment in which the values supplied from the memory 20 are fed via the control unit 33 to the control unit 34 which performs the conversion into control signals for the linear motors 28.

By applying or removing wax, the dental technician may now correct the individual teeth at the plaster models 24 in order to bring about a distribution of load as uniform as possible on the teeth and jaws during chewing.

What is claimed is:

1. Apparatus for reproducing jaw movements of a patient comprising:

upper and lower jaw plates for placement in the mouth of a patient against the upper and lower jaws of the patient;

at least one distance measuring means secured at said upper and lower jaw plates for measuring distances between said upper and lower jaw plates in the mouth of a patient, said at least one distance measuring means being located within the mouth of the patient when said upper and lower jaw plates are placed in the mouth of the patient;

storage means for said measured distances; and an articulator carrying models of the upper and lower jaws, said upper and lower jaw plates being mountable in said models of the upper and lower jaws, wherein said articulator comprises:

a stationary receiving unit for the model of the upper jaw;

a control unit; and a mobile receiving unit for the model of the lower jaw cooperating with said control unit capable of moving with several degrees of freedom;

said articulator, said storage means and said models of the upper and lower jaws cooperating to reproduce the combinations of distances between the defined points of the lower and upper jaws measured by said at least one distance measuring means.

2. Apparatus according to claim 1 comprising at least three distance measuring means.

3. Apparatus according to claim 1 wherein said at least one distance measuring means has one common transmitter which is secured to the upper jaw plate and at least three receivers which are secured to the lower jaw plate.

4. Apparatus for reproducing jaw movements of a patient comprising:

upper and lower jaw plates for placement in the mouth of a patient against the upper and lower jaws of the patient;

at least three distance measuring means having one common transmitter which is secured to the upper jaw plate and at least three receivers which are secured to the lower jaw plate for measuring the distances between defined points on said upper and lower jaw plates in the mouth of the patient;

storage means for said measured distances;

an articulator carrying models of the upper and lower jaws, said upper and lower jaw plates being mountable in said models of the upper and lower jaws, wherein said articulator comprises:

a stationary receiving unit for the model of the upper jaw;

a control unit; and a mobile receiving unit for the model of the lower jaw cooperating with said control unit capable of moving with several degrees of freedom; and a comparator to which said control unit is connected for comparing the distances measured by said distance measuring means and stored in said storage means to the corresponding distances separating said upper and lower jaw plates mounted on said upper and lower jaw models carried by said articulator and for adjusting the differences in said compared distances to zero by actuation of the control unit; said articulator, said storage means, said comparator and said models of the upper and lower jaws cooperating to reproduce the combinations of distances between the defined points of the lower and upper jaws measured by said at least three distance measuring means.

5. Apparatus for reproducing jaw movements of a patient comprising:
   upper and lower jaw plates for placement in the mouth of the patient against the upper and lower jaws of the patient;
   at least three distance measuring means having one common transmitter which is secured to the upper jaw plate and at least three receivers which are secured to the lower jaw plate for measuring the distances between defined points on said upper and lower jaw plates in the mouth of the patient, said at least three distance measuring means being located within the mouth of the patient when said upper and lower jaw plates are placed in the mouth of the patient;
   storage means for said measured distances;
   an articulator carrying models of the upper and lower jaws, said upper and lower jaw plates being mountable in said models of the upper and lower jaws, wherein said articulator comprises:
      a stationary receiving unit for the model of the upper jaw;
      a mobile receiving unit for the model of the lower jaw;
      drive units cooperating with said mobile receiving unit; and
      a control unit which contains a computer circuit which converts the distances measured in the mouth of the patient into control signals for said drive units in order to move the mobile receiving unit;
   said articulator, said storage means and said models of the upper and lower jaws cooperating to reproduce the combinations of distances between the defined points of the lower and upper jaws measured by said at least three distance measuring means.

6. Apparatus for reproducing jaw movements of a patient comprising:
   upper and lower jaw plates for placement in the mouth of a patient against the upper and lower jaws of the patient;
   at least three distance measuring means having one common transmitter which is secured to the upper jaw plate and at least three receivers which are secured to the lower jaw plate for measuring the distances between defined points on said upper and lower jaw plates in the mouth of the patient, said at least three distance measuring means being located within the mouth of the patient when said upper and lower jaw plates are placed in the mouth of the patient;
   storage means for said measured distances;
   an articulator carrying models of the upper and lower jaws, said upper and lower jaw plates being mountable in said models of the upper and lower jaws, wherein said articulator comprises:
      a stationary receiving unit for the model of the upper jaw;
      a control unit;
      a mobile receiving unit for the model of the lower jaw cooperating with said control unit capable of moving with several degrees of freedom;
      a base plate; and
      linear acting drive means connected to said mobile receiving unit and said base plate for moving said mobile receiving unit as directed by said control unit;
   said articulator, said storage means and said models of the upper and lower jaws cooperating to reproduce the combinations of distances between the defined points of the lower and upper jaws measured by said at least three distance measuring means.

7. A system for reproducing jaw movements in upper and lower jaw models situated on a stand comprising:
   measuring means, placeable entirely in the mouth of a patient, for producing electrical signals indicative of the relative movement of the upper and lower jaws;
   storage means for storing said signals indicative of jaw movement;
   articulatable stand means, supporting said upper and lower jaw models and comprising
      mechanisms for moving said lower jaw model;
      a stationary support means for said upper jaw model;
      a movable support means for said lower jaw model attached to said mechanisms; and
   control means responsive to said stored signals and cooperating with said mechanisms for moving said upper and lower jaw models relative to one another in accordance with said stored signals, thereby reproducing in the upper and lower jaw models the movement of said patient's jaw.

8. A system as in claim 7 wherein said measuring means measures distances and produces signals over an interval of time indicative of displacements between at least one point on the upper jaw and at least one point on the lower jaw.

9. A system as in claim 7 wherein said measuring means comprises a transmitter and receiver means.

10. A system as in claim 9 further comprising upper and lower jaw plates removably insertable into the mouth of a patient for carrying respectively a first and second part of said transmitter and receiver means.

11. A system for reproducing jaw movements in upper and lower jaw models situated on a stand comprising:
   upper and lower jaw plates removably insertable, alternatively, into the mouth of a patient at the upper and lower jaws respectively or into the models of the upper and lower jaws respectively;
   transmitter and receiver means having a first and second part, said first part being secured to said upper jaw plate and said second part being secured to said lower jaw plate, said first and second parts cooperating to produce signals indicative of displacements over an interval of time between at least one point on the upper jaw plate and at least one point on the lower jaw plate;
   storage means for said signals produced over an interval of time while said upper and lower jaw plates are inserted into the mouth of a patient;
   articulatable stand means supporting said models of the upper and lower jaw comprising:
      a stationary support means for said upper jaw model;
      a movable support means for said lower jaw model; and
      a mechanism for moving said movable support means; and
   comparison and control means cooperating with said storage means and said articulatable stand means for comparing with said signals stored in said storage means corresponding signals indicative of the displacements between the same said at least one point on the upper jaw plate and said at least one point on the lower jaw plate when said plates are inserted into the models of the upper and lower jaws, and for controlling over an interval of time the relative positions of said upper and lower jaw models, said mechanism being responsive to said comparison and control means so that said latter displacements are equal to the displacements measured when said jaw plates were in the mouth of the patient, thereby reproducing said jaw movements.

12. A system as in claim 11 wherein said transmitter means comprises a single transmitter and said receiver means comprises three separate receivers disposed so as to be located at the corners of an approximately equilateral triangle.

13. A system as in claim 11 wherein said mechanism comprises a plurality of linear motors disposed between said movable support means and a stationary base plate.

14. Apparatus for reproducing jaw movements of a patient comprising:
   upper and lower jaw plates for placement in the mouth of a patient against the upper and lower jaws of the patient;
   at least one distance measuring means secured at said upper and lower jaw plates for measuring distances between said upper and lower jaw plates in the mouth of a patient;
   storage means for said measured distances; and
   an articulator carrying models of the upper and lower jaws, said upper and lower jaw plates being mountable in said models of the upper and lower jaws, wherein said articulator comprises:
   a stationary receiving unit for the model of the upper jaw;
   a control unit; and
   a mobile receiving unit for the model of the lower jaw cooperating with said control unit capable of moving said several degrees of freedom; and
   a comparator to which said control unit is connected for comparing the distances measured by said distance measuring means and stored in said storage means to the corresponding distances separating said upper and lower jaw plates mounted on said upper and lower jaw models carried by said articulator and for adjusting the differences in said compared distances to zero by actuation of the control unit;
   said articulator, said storage means and said models of the upper and lower jaws cooperating to reproduce the combinations of distances between the defined points of the lower and upper jaws measured by said at least one distance measuring means.

15. Apparatus according to claims 2, 3, or 1 further comprising drive units cooperating with said mobile receiving unit and wherein said control unit contains a computer circuit which converts the distances measured in the mouth of the patient into control signals for said drive units in order to move the mobile receiving unit.

16. Apparatus according to claims 2, 3 or 1 further comprising:
   a base plate; and
   linear acting drive means connected to said mobile receiving unit and said base plate for moving said mobile receiving unit as directed by said control unit.

17. A system as in claim 12 wherein said mechanism for moving said movable means comprises six linear motors, said linear motors attached at one end adjacent to points defining vertices of a triangle on said stationary base plate and attached at the other end adjacent to points defining vertices of a triangle on said movable support means whereby said lower jaw model can move relative to said upper jaw model with six degrees of freedom.

18. A system as in claim 17 wherein said triangles on said stationary base plate and on said movable support means are approximately equilateral and two linear motors are attached adjacent to each vertex of each triangle, the ends of the linear motors whose opposite ends are attached adjacent to the same vertex being attached to different vertices.

19. Apparatus according to claim 14 comprising at least three distance measuring means.

20. Apparatus according to claim 14 wherein said at least one distance measuring means has one common transmitter which is secured to the upper jaw plate and at least three receivers which are secured to the lower jaw plate.

* * * * *